United States Patent [19]

Loertscher

[11] Patent Number: 4,887,592
[45] Date of Patent: Dec. 19, 1989

[54] CORNEA LASER-CUTTING APPARATUS

[76] Inventor: Hanspeter Loertscher, 100 Ocean Lane Dr., #207, Key Biscayne, Fla. 33149

[21] Appl. No.: 56,711

[22] Filed: Jun. 2, 1987

[51] Int. Cl.$^4$ .............................................. A61N 5/06
[52] U.S. Cl. ........................................ 606/5; 128/395; 219/121.6; 219/121.7; 219/121.78
[58] Field of Search ............. 128/303.1, 362, 395–398; 219/121 L, 121 LP, 121 LQ, 121 LR, 121 LJ, 121.6, 121.78, 121.79, 121.80, 121.7

[56] References Cited

U.S. PATENT DOCUMENTS

| | | | |
|---|---|---|---|
| 3,096,767 | 7/1963 | Gresser et al. | 128/303.1 |
| 3,419,321 | 12/1968 | Barber et al. | 219/121 LR |
| 3,534,462 | 10/1970 | Cruicklshank et al. | 219/121 LR |
| 3,710,798 | 1/1973 | Bredemeier | 128/303.1 |
| 3,848,970 | 12/1974 | Goodell | 219/121 LR |
| 3,947,780 | 3/1976 | Rice et al. | 372/18 |
| 4,123,143 | 10/1978 | Vachin et al. | 128/303.1 |
| 4,275,288 | 6/1981 | Makosch et al. | 219/121 LR |
| 4,461,294 | 7/1984 | Baron | 128/303.1 |
| 4,538,608 | 9/1985 | L'Esperance, Jr. | 128/303.1 |
| 4,628,416 | 12/1986 | Deway | 128/303.1 |
| 4,648,400 | 3/1987 | Schneider et al. | 128/303.1 |
| 4,665,913 | 5/1987 | L'Esperance, Jr. | 128/303.1 |
| 4,718,418 | 1/1988 | L'Esperance, Jr. | 219/121 LR |

OTHER PUBLICATIONS

"Polarization Effects of Axicons" (Applied Optics, vol. 18, No. 5, Mar. 1, 1979).
"Linear, Annular, and Radial Focusing With Axicons and Applications to Laser Machining" (Applied Optics, vol. 17, No. 10, May 15, 1978).
"The Axicon: A New Type of Optical Element" (Journal of the Optical Society of America, vol. 44, No. 8, Aug. 1954).
Advertisement for a Model 294 Erbium: YAG Laser Offered For Sale by the Quantronix Corp.
"Limbectomies, Keratectomies, and Keratostomies Performed With a Rapid-Pulsed Carbon Dioxide Laser", American Journal of Ophthalmology, vol. 71, No. 6, Jun. 1971.
"Excimer Laser Ablation of the Cornea and Lens", American Journal of Ophthalmology, vol. 92, No. 6, Jun. 1985.

Primary Examiner—Lee S. Cohen
Assistant Examiner—David Shay
Attorney, Agent, or Firm—Finnegan, Henderson, Farabow, Garrett & Dunner

[57] ABSTRACT

A cornea laser-cutting apparatus adapted for use in cutting out a cornea of patient's or donor's eye in full thickness cornea transplanting surgery or keratoplasty. The cornea laser-cutting apparatus comprises an HF or Er-YAG laser source and a projection optical system for converging laser beams radiated from the laser source in a ring-like shape on the cornea, and includes an axicon lens or mirror movably mounted for varying the size of the ring-like shape.

15 Claims, 4 Drawing Sheets

CORNEA LASER-CUTTING APPARATUS

BACKGROUND OF THE INVENTION

This invention relates to a microsurgery apparatus and, more particularly, a cornea laser-cutting apparatus adapted for use in cutting out a cornea in full thickness during cornea transplant surgery or keratoplasty.

Despite advances in corneal preservation and transplantation, postoperative astigmatism remains the most important complication limiting visual acuity after penetrating keratoplasty. The major contributing factor appears to be the difficulty in creating a truly round recipient opening.

Conventionally, mechanical cutting methods have been applied to such cornea transplanting surgery or keratoplasty by means of a trepan and corneal scissors. However, these mechanical cutting methods are apt to cause strain and/or deformation on the cornea being removed, and often result in incorrect sizing of a donor cornea to a recipient opening. As a result, patients with corneas which have been transplanted from a donor's eye experience astigmatism.

In addition, a two step surgical operation is required in the conventional method using a trepan and corneal scissors so that it takes an ophthalmologist a very long time to carry out the cornea transplantation or keratoplasty.

Further, an ophthalmologist is required to learn a particularly delicate, skilled technique to cut out corneas using the prior art methods.

Current techniques of punching the donor from the endothelial side generally result in a fairly circular button. Sewing such a circular button into an oval hole, however, results in different amounts of corneal tissue along the major and minor axes of the elliptical opening, and in astigmatism. These tissue differences may be temporarily compensated for by selective suture removal. Ultimately, however, sutures loosen and must be removed. Variations in the shape of the recipient opening from patient to patient are a likely explanation for the sometimes substantially different amounts of astigmatism experienced by one surgeon using the same technique.

Noncontact trephination of the cornea, if possible, would minimize distortion and enchance the likelihood of producing a circular opening. The application of lasers which cut the cornea provide the potential for such a trephine system.

Excimer lasers have been investigated in the past to produce linear corneal incisions. The argon fluoride excimer laser emitting at 193 nm has been shown to produce sharp, smooth-walled corneal cuts. More recently, the hydrogen fluoride laser emitting at 2.9 $\mu$m, which corresponds to the peak absorption wavelength of water, has been experimentally used to produce linear corneal incisions. Laser trephination, achieved by focusing the beam into a ring, has been proposed as a method for drilling large diameter holes for industrial applications. The axicon, a diverging prismatic lens, has been used for this purpose and has been studied extensively since its discovery by McLeod in 1954. An axicon system previously was used by Beckman and associates to study corneal trephination with a carbon dioxide laser. This experimentation is described in an article entitled "Limbectomies, Keratectomies, and Kerastomies Performed With a Rapid-Pulsed Carbon Dioxide Laser" in American Journal of Ophthalmology, Vol. 71, No. 6, (June 1971). In this article, Beckman et al describe the use of an axicon lens in combination with a focusing lens to form an "optical trephine" and perform various corneal experiments with animal's. The diameter of the trephine was governed by the focal length of the focusing lens in these experiments. Therefore, to vary the size of the circular beam, it was necessary to change the focusing lens in this arrangement, which in addition varied the width of the annulus. This would require a time consuming process to adjust the diameter of the trephine for each patient or donor. In addition, the optical system is more complex than that of the present invention, and requires the use of multiple focusing lenses of different focal length.

SUMMARY OF THE INVENTION

Accordingly, one object of the present invention is to provide a cornea laser cutting apparatus which substantially eliminates strain and/or deformation on a cut-out cornea.

Another object of the present invention is to provide a cornea laser-cutting apparatus which is capable of cutting out a cornea non-contactually.

Yet another object of the present invention is to rapidly change the beam size of a cornea lase-cutting apparatus to adjust for different corneas and patients.

Additional objects and advantages will be obvious from the description which follows or may be learned by practice of the invention.

To achieve the foregoing objects and advantages, the cornealaser cutting apparatus of the present invention comprises means for generating laser beams; and means for projecting the laser beams onto a cornea for cutting the cornea, said projecting means defining an optical path, and including means for converging the laser beams, and axicon optical means for projecting the beam in a ring-like, i.e., annular shape on the cornea an varying the size of the ringlike shape.

Preferably, the converging means includes a focusing lens. It is also preferred that the axicon optical means include at least one axicon lens mounted for movement with respect to the optical path of said projecting means.

The projecting means preferably includes beam expander means for enlarging the radius of the laser beam from the generating means. The generating means may include an infrared pulse laser beam generator with a preferred wavelength of about 2.9 $\mu$m.

The apparatus may also include aiming means for projecting ring-like, i.e., annular visible laser beams on the cornea substantially coincident with the laser beams projected by said axicon means. The optical path of the aiming means preferably overlaps with a part of the optical path of said projecting means. Preferably, the aiming means includes a visible laser beam source, and a mirror obliquely interposed between said beam expander beams and said converging means for reflecting the visible laser beams and allowing the laser beams from the generating means to pass therethrough.

BRIEF DESCRIPTION OF THE DRAWINGS

The accompanying drawings, which are incorporated in and constitute a part of the specification, illustrate several embodiments of the invention, and together with the description, serve to explain the principles of the invention. Of the drawings.

DETAILED DESCRIPTION OF THE PREFERRED EMBODIMENTS

Reference will now be made in detail to the present preferred embodiment of the invention, examples of which are illustrated in the accompanying drawings.

Figure 1:
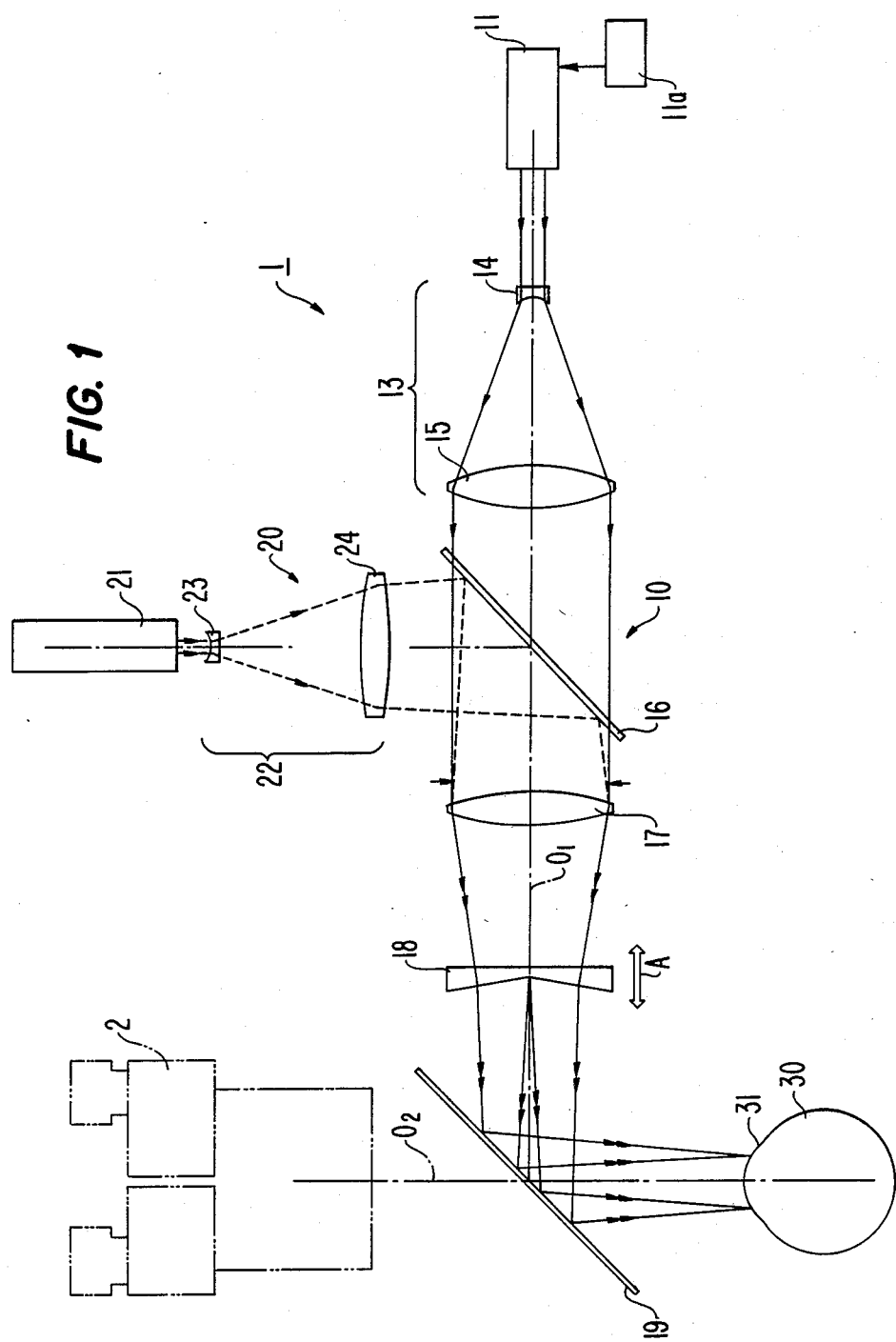
FIG. 1 shows an optical system arrangement of a first embodiment of a cornea laser-cutting apparatus in accordance with the present invention.

As shown in FIG. 1, an optical delivery system of a cornea laser-cutting apparatus of the invention includes a laser beam projection system 10 and an aiming system 20.

The laser beam projection system 10 is provided with a laser source 11 which generates a laser beam that is capable of ablating the tissue of a living organ, i.e., a cornea. Lasers which meet the requirements described above are now available, e.g., HF (Hydrogen Fluoride) lasers and Er-YAG (Erbium-Yttrium Aluminum Garnet) lasers that are infrared pulse lasers having wavelengths of about 2.0 to about 3.0 μm, and preferably about 2.9 μm. The laser source 11, therefore may be a HF laser source. The laser source 11 is connected to a radiation control switch 11a. When the control switch 11a turns on, the HF laser source generates infrared pulse beams.

The output laser beams from the HF laser source 11 are enlarged in radius through a beam expander 13, which comprises a concave lens 14 and a convex lens 15. The laser beams from the convex lens 15 are made parallel and are in turn projected toward a diverging prismatic lens (axicon lens) 18 through a cold mirror 16 and a condensing (focusing) lens 17. The axicon lens 18 has a prism-like reverse conical shape in sectional view. The outer edge thereof (prism base) is larger in width than the optical axis portion thereof, as shown in FIG. 1. Due to the prism function of the axicon lens 18, the output beams therefrom are made ring-like or annular. The ring-like, i.e., annular beams then are converted on a cornea 31 of an eye 30 (a patient's eye or a donor's eye) after reflection by a dichroic mirror 19. As a result, the cornea 31 is circularly cut out by the laser beam energy.

The inventors have discovered that the sharpness and the accuracy of the cutting greatly depend on the width of the ringlaser beam converged on the cornea, i.e. it is desirable to set the width of the ring-like or annular laser beam to be narrow. For this purpose, the beam expander 13 contributes to make the NA (Numerical Aperture) of the focusing lens 17 so large that the incident laser beam becomes large in diameter.

It is necessary to vary the cornea cutting diameter ordinarily from 5 mm to 8 mm in cornea transplanting surgery or keratoplasty. To this end, the axicon lens 18 preferably is mounted to be movable along the optical axis $O_1$, in the directions indicated by an arrow "A."

Figure 3:
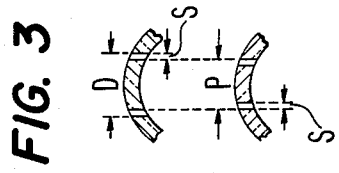
FIG. 3 is a cross-sectional view of cuts typically necessary for a donor and recipient cornea.

FIG. 3 illustrates the precise measurement required to cut a donor cornea and a patient cornea for proper fit. The close tolerances involved make it extremely difficult using manual cutting techniques.

Variations in the size of donor and patient corneas further increase the need for ability to vary the diameter of the cuts.

Figure 2:
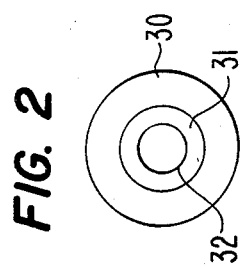
FIG. 2 is a plan view of a laser beam projected onto a cornea of an eye.

The aiming system 20 (FIG. 2) includes a He-Ne laser source 21, a beam expander 22 and the cold mirror 16. The He-Ne laser source 21 generates visible laser beams. The beam expander 22 has a concave lens 23 and a convex lens 24. The cold mirror 16 only reflects incident He-Ne laser beams, while HF laser beams pass therethrough.

Ne-He laser beams from the laser source 21 are enlarged in diameter by the expander 22, whose output laser beams, in turn, are projected to the condensing (focusing) lens 17 after reflection by the cold mirror 16. Accordingly, the He-Ne laser beams from the condensing lens 17 travel along the same optical path as the HF laser beam For observing the cornea and the annular He-Ne laser beams projected thereon, the cornea laser-cutting apparatus is provided with an operation microscope 2, indicated by phantom line in FIG. 1. The operation microscope is well known in the ophthalmology field. Therefore, its detailed explanation is omitted.

The optical axis $O_2$ of the operation microscope 2 is adjusted to be coincident with that ($O_1$) of the cornea laser-cutting apparatus. The dichroic mirror 19 functions as a half mirror for the He-Ne laser beams, but as a complete mirror for the HF laser beams. An operator can determine an optimum diameter size of a cornea by observing the He-Ne laser beams projected thereon through the operation microscope 2.

The cornea transplanting surgery or keratoplasty can be carried out by using the cornea laser-cutting apparatus as hereinbelow explained.

Visible aiming laser beams from the He-Ne laser source 21 are projected on a cornea of a patient or donor through the beam expander 22, the cold mirror 16, the condensing lens 17, the axicon lens 18 and the dichroic mirror 19.

The visible aiming laser beam projected on a cornea is ring-like or annular in shape, which can be observed through the operation microscope 2. Focus of the projected laser beam is adjustable by moving the cornea laser-cutting apparatus and the operation microscope in a body along with the optical axis $O_2$.

Next, the axicon lens 18 is moved along the optical axis $O_1$ so that the annular laser beam diameter is adjusted to be optimum in size.

After the annular laser beam diameter has been set at an optimum size by means of the aiming system 20 and the operation microscope 2, the control switch 11a is turned on and the HF laser source 22 generates the HF (invisible) pulse laser beams.

Then, the HF pulse laser beams are projected onto the cornea through the beam expander 13, the cold mirror 16, the condensing lens 17, the axicon lens 18 and the dichroic mirror 19, respectively, to cut out the cornea.

Figure 4:
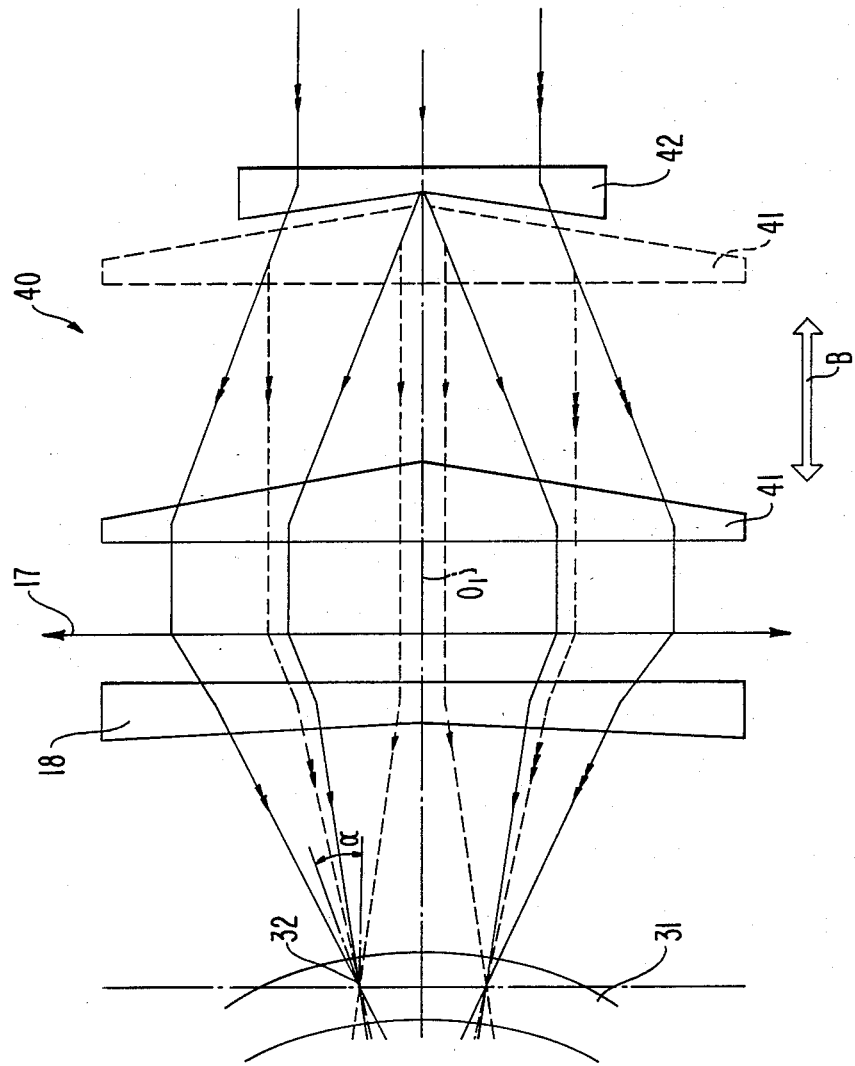
FIG. 4 shows an optical system arrangement of a second embodiment of the invention.

FIG. 4 shows a second embodiment of an optical system in which a variable diverging beam expander 40 is positioned in place of the beam expander 13 of the embodiment (FIG. 1)

For the sake of simplicity, the cold mirror 16 and other optical components are omitted from the drawing and the focusing lens 17 is illustrated by an arrow line.

The beam expander 40 includes a fixed axicon lens 42, the prism base of which is outside of the optical axis $O_1$, and an axially movable axicon lens 41, the prism base of which is aligned with the axis $O_1$.

When the axicon lens 41 moves along the axis $O_1$ in the directions of the arrow "B," an incident angle with respect to the cornea 31 varies in response to the movement of the axicon lens, while the trephination diameter remains unchanged.

Figure 5A:
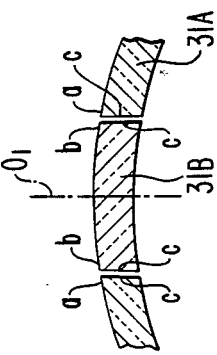
FIG. 5A is a cross-sectional view of the cuts of a donor cornea and a patient's eye using the embodiment of FIG. 1.
Figure 5B:
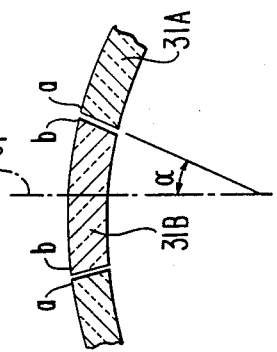
FIG. 5B is a cross-sectional view of a cornea cut using the embodiment of FIG. 4.

By optimizing such an incident angle, healing and postoperative corneal deformations are greatly improved. Namely, in case of the the first embodiment, the cutting end is parallel to the axis $O_1$, as shown in FIG. 5A, so that height adjustment at the edges between donor's and patient's corneas cannot be carried out easily in keratoplasty. However, with the present embodiment, either a donor's or a patient's cornea is conically cut, as shown in FIG. 5B. Thus, the height adjustment, if an incident angle $\alpha$ is properly set, can be carried out more easily and precisely.

As an alternative of the second embodiment, the beam expander 40 may be positioned between the cold mirror 16 and the focusing lens 17 (FIG. 1). This is particularly useful in a large size trephination with the same practical advantage as in the second embodiment.

Figure 6:
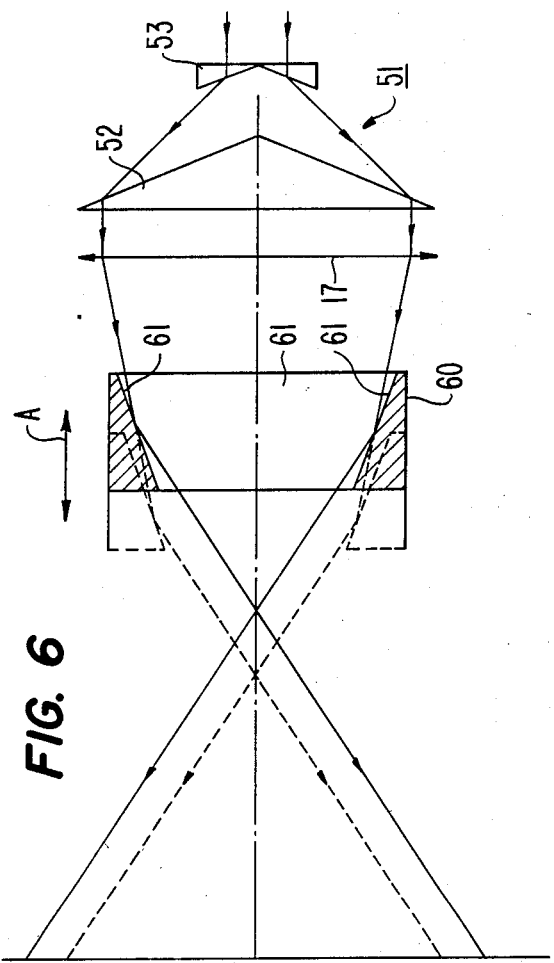
FIG. 6 is an optical arrangement of a third embodiment of the invention.
Figure 7:
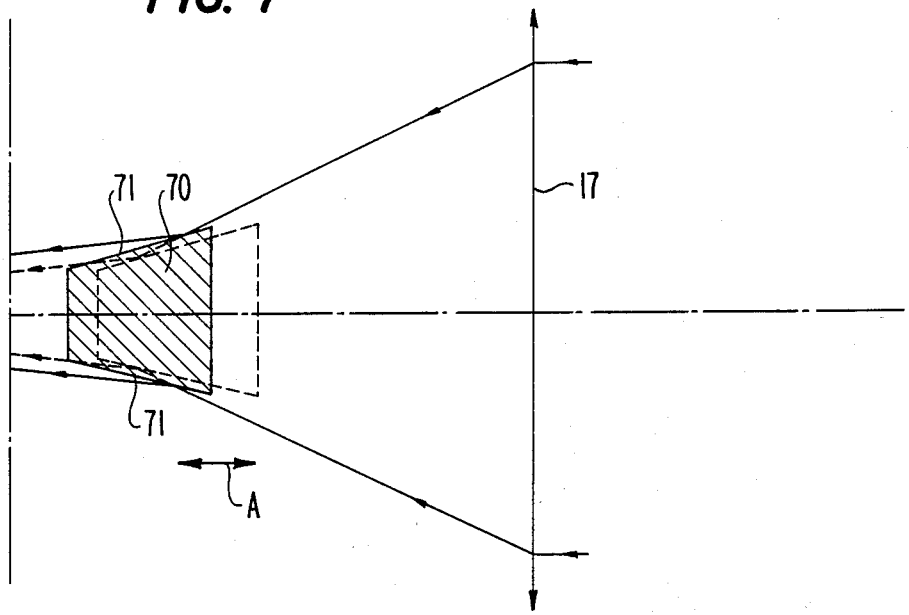
FIG. 7 is an optical arrangement of a fourth embodiment with an axially movable axicon mirror.

FIGS. 6 and 7 show third and fourth embodiments, respectively.

The third embodiment optical system includes a fixed beam expander 51, a focusing lens 17, and an axially movable axicon mirror 60. In this embodiment, the fixed beam expander 51 is directly optically connected to the laser source 11 (not shown) and performs the same function as the beam expander 13 (FIG. 1). In addition, the cold mirror 16 is preferably positioned between the laser source 11 and the fixed beam expander 51.

As an alternative, the cold mirror 16 may also be positioned between the fixed beam expander 51 and the focusing lens 17.

The beam expander 51 includes a diverging axicon lens 53 and a converging axicon lens 52. The movable axicon mirror 60 has an inner mirror surface 61. In response to its movement along the axis in the directions of the arrow "A," the trephination diameter varies.

The fourth embodiment of FIG. 7 shows an axially movable axicon mirror 70 with a mirror surface 17. The axicon mirror 70 is positioned in place of the axicon lens 18 shown in FIG. 1, and performs substantially the same function as the latter.

Figure 8:
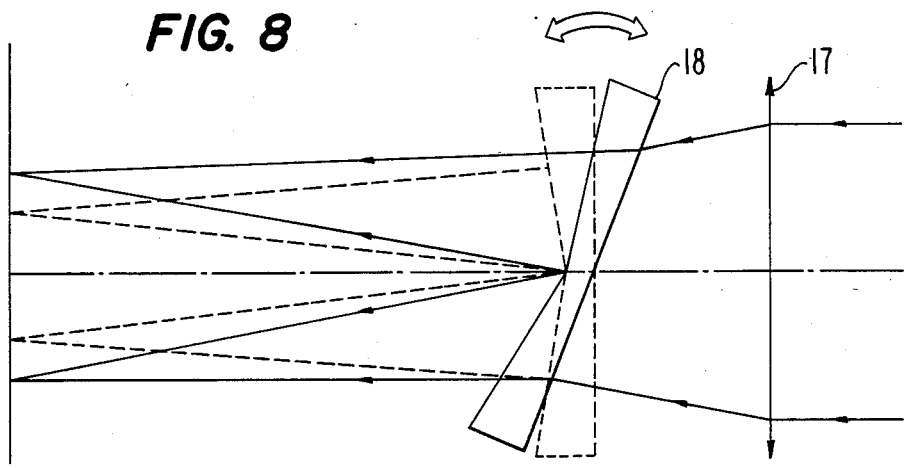
FIG. 8 shows an optical arrangement of a fifth embodiment having a tiltable axicon lens.

With reference to FIG. 8, there is shown a fifth embodiment optical system in which an axicon lens 18 is set to be tiltable. In response to the tilt of the axicon 18, an oval or elliptical cutting can be performed in a recipient's cornea, which allows for correction of pre-existing astigmatism.

When the axicon lens 18 rotates around the axis perpendicular to the paper plane, as shown in FIG. 8, the cutting shape becomes oval or elliptical.

Experimental Results

The following is a description of an actual experiment carried out by the inventors using an HF laser. A pulsed hydrogen fluoride laser, model PCLI, which was modified by the manufacturer (Helios Inc., Longmont, Colo.) to improve beam homogeneity and to increase laser output was utilized. The originally rectangular beam cross section (5 mm $\times$ 10 mm) was changed into a quadratic cross section (5 mm $\times$ 5 mm), and the maximum pulse energy at 10 Hz repetition rate was increased from 50 mJ to 130 mJ. An unstable resonator was used to minimize beam divergence and beam width in the focal plane.

An optical system (manufactured by Tokyo Optical Co., Ltd., Tokyo, Japan) was utilized to focus the laser pulses into an annulus on the anterior corneal surface (FIG. 1). An axicon, which was placed between the focusing lens and its focal plane, diverged the otherwise produced focal spot into an annulus. The diameter of the annulus was varied from 5 to 7 mm by altering the position of the axicon along the beam axis. The system was aligned to produce the most regular and narrowest ring on thermal paper which was placed in the focal plane of the lens. The width of the annulus varied from 100 um to 150 um over 340 degrees, and was only 50 um over 20 degrees. The correct position of the cornea relative to the invisible laser annulus was determined with a biomicroscope. The microscope was rigidly mounted and its light path was coupled into the laser beam by means of a dichroic mirror. A reticule in one eyepiece indicated the position of the annulus.

The donor eyes whose corneas were judged not suitable for transplantation were obtained through the Florida Lions Eye Bank. The corneal epithelium was removed with a cotton-tipped applicator prior to irradiation. The eyes were placed in a suction glove holder which was mounted on a micrometer stage. The position of the globe was adjusted to focus the reticule in the eyepiece on the anterior corneal surface. Saline was infused through an 20-gauge needle inserted through pars plana to maintain an intraocular pressure of 20 mm Hg. The laser was run at a fixed repetition rate of 10 Hz and adjusted to deliver 100 mJ pulse energy, which corresponded to 55 mJ measured on the cornea. The number of pulses delivered to the cornea could be selected by an electro-mechanical beam shutter. Trephinations of 5 mm and 6.5 mm diameter were produced with 20, 50, 70, 100 and 120 pulses. After irradiation, corneal buttons with an adjacent scleral rim were moved and placed in glutaraldehyde for 24 hours. The buttons were bisected. One half was embedded in paraffin, transversely sectioned, routinely processed for light microscopy, and stained with hematoxylin and eosin. The second half of the button was dehydrated in graded alcohols and acetone, critical point dried, and coated for examination in a JEOL 35C scanning electron microscope.

A 90% deep corneal trephination with a 6.5 mm diameter was produced by 70 pulses, 55 mJ per pulse, 5 J/cm2 radiant exposure, delivered at 10 Hz repetition rate. With biomicroscopy a uniform tissue excision was narrower and the depth only about 40% corneal thickness. Histologically, corneal stromal edema was present adjacent to the excision site. A darkly staining zone, approximately 10 um wide and indicative of thermal damage was noted and the lamellar stromal architecture was disturbed within 100 um of the excision. The underlying endothelium appeared to be intact. A slightly uneven depth of the excision was seen under the scanning electron microscope. The excision to the left was about 90% deep, while the one to the right was only about 50% corneal thickness.

A complete excision of a corneal button could not be obtained with this laser trephine system. When 100 and more pulses were delivered, focal leakage of aqueous into the trough of the trephination was observed after 75 to 85 pulses. Subsequent pulses no longer excised tissue, but evaporated the leaking aqueous.

This experiment demonstrated the feasibility of using a pulsed hydrogen fluoride laser to perform circular corneal trephinations.

Although the pulsed hydrogen fluoride laser was used to demonstrate the feasibility of a laser trephine, other cutting lasers, either mid-infrared lasers such as erbium: YAG lasers, or the ultraviolet 193 nm excimer lasers may be used as well.

The invention may be embodied in other specific forms without departing from the spirit of essential characteristics thereof. The present embodiment is therefore to be considered in all respects as illustrative and not restrictive, the scope of the invention being indicated by the appended claims rather than by the foregoing description and all changes which comes within the meaning and range of equivalency of the claims are therefore intended to be embraced therein.

What we claim is:

1. A cornea laser-cutting apparatus comprising:
    means for generating laser beams;
    means for projecting said laser beams onto a cornea to cut the cornea, said projecting means having an optical axis thereof;
    means for converging and focusing the laser beams onto an imaging plane substantially coincident with the surface of the cornea;
    axicon lens means, disposed between said converging means and said imaging plane along said optical axis, for converting the laser beams exiting from said converging means into annularly shaped laser beams impinging on the cornea; and
    means for moving said axicon lens means along said optical axis to change the diameter of the annularly shaped laser beams impinging on the cornea.

2. A cornea laser-cutting apparatus as in claim 1, wherein said converging means includes a focusing lens.

3. A cornea laser-cutting apparatus as in claim 1, wherein said generating means includes an infrared pulsed laser beam generator.

4. A cornea laser-cutting apparatus as in claim 3, wherein said generating means includes an HF laser source.

5. A cornea laser-cutting apparatus as in claim 3, wherein said generating means includes an Er-YAG laser source.

6. A corneal laser-cutting apparatus as in claim 1, wherein the wavelength of laser beams generated by said laser beam generator means is about 2.9 $\mu$m.

7. A cornea laser-cutting apparatus as in claim 1, wherein said generating means includes an ultraviolet pulsed laser beam generator.

8. A cornea laser-cutting apparatus as in claim 7, wherein the wavelength of beams generated by the ultraviolet pulsed laser beam generator is about 193 nm.

9. A cornea laser-cutting apparatus as in claim 7, wherein said ultraviolet pulsed laser beam generator is an excimer laser.

10. A cornea laser-cutting apparatus as in claim 1, wherein said projecting means further includes beam expander means, disposed between said axicon lens means and said generating laser means, for enlarging the radius of the laser beams, and for projecting the laser beams toward said converging means in a path parallel to said optical axis.

11. A cornea laser-cutting apparatus as in claim 10 further aiming means for projecting annularly shaped visible laser beams on the cornea substantially coincident with the laser beams projected by said axicon means.

12. A cornea laser-cutting apparatus as in claim 11, wherein the optical axis of the aiming means overlaps with a portion of said optical axis of said projection means.

13. A cornea laser-cutting apparatus as in claim 12, wherein said aiming means includes a visible laser beam source, and mirror means, obliquely interposed between said beam expander means and said converging means, for reflecting the visible laser beams and allowing the laser beams from said laser generating means to pass therethrough.

14. A cornea laser-cutting apparatus as in claim 10, wherein the beam expander means includes a variable diverging beam expander.

15. A cornea laser-cutting apparatus as in claim 14, wherein the beam expander includes a fixed axicon lens and an axially movable axicon lens for varying the angle of incidence of the laser beam on the cornea.

* * * * *

UNITED STATES PATENT AND TRADEMARK OFFICE
CERTIFICATE OF CORRECTION

PATENT NO. : 4,887,592
DATED : December 19, 1989
INVENTOR(S) : Hanspeter Loertscher It is certified that error appears in the above-identified patent and that said Letters Patent is hereby corrected as shown below:

Claim 10, column 8, line 22, change "generating laser means" to read --generating means--.

Claim 11, column 8, line 27, delete "aiming" and substitute therefore --including aiming--.

Signed and Sealed this

Thirtieth Day of June, 1992

Attest:

DOUGLAS B. COMER

*Attesting Officer*     *Acting Commissioner of Patents and Trademarks*